United States Patent [19]

MacGregor

[11] Patent Number: 4,934,381
[45] Date of Patent: Jun. 19, 1990

[54] POROUS CARBON PACEMAKER ELECTRODE

[76] Inventor: David C. MacGregor, 10421 SW. 89th Ave., Miami, Fla. 33176

[21] Appl. No.: 711,759

[22] Filed: Mar. 14, 1985

Related U.S. Application Data

[63] Continuation of Ser. No. 375,442, May 6, 1982, abandoned, which is a continuation-in-part of Ser. No. 226,366, Jan. 19, 1981, abandoned, which is a continuation of Ser. No. 824,296, Aug. 15, 1977, Pat. No. 4,281,669, which is a continuation-in-part of Ser. No. 683,382, May 5, 1976, Pat. No. 4,101,984.

[51] Int. Cl.$^5$ .......................... A61N 1/05; A61N 1/06
[52] U.S. Cl. ............................. 128/784; 128/419 P
[58] Field of Search ................................ 128/784–786, 128/419 P, 92 C

[56] References Cited

U.S. PATENT DOCUMENTS

| | | | |
|---|---|---|---|
| 3,590,822 | 7/1971 | Ackerman | 128/786 |
| 3,757,789 | 9/1973 | Shanker | 128/786 |
| 3,855,638 | 12/1974 | Pilliar | 128/92 C X |
| 4,011,861 | 3/1977 | Enger | 128/419 P X |
| 4,030,508 | 6/1977 | Thalen | 128/786 |
| 4,052,754 | 10/1977 | Homsy | 128/419 P X |
| 4,149,542 | 4/1979 | Thoren | 128/419 P X |
| 4,281,668 | 8/1981 | Richter et al. | 128/784 |

*Primary Examiner*—Ronald L. Frinks
*Attorney, Agent, or Firm*—Shoemaker and Mattare, Ltd.

[57] ABSTRACT

An endocardial pacemaker electrode has a surface region constructed of carbon and having pores for receiving the growth of tissue therein to permit the fixation of the electrode in the atrium or other location by the ingrowth of adjacent tissue. By fixing the location of the electrode, low stimulation thresholds and a consistent magnitude of sensed endocardial signal are maintained.

7 Claims, 2 Drawing Sheets

POROUS CARBON PACEMAKER ELECTRODE

REFERENCE TO RELATED APPLICATIONS

This application is a continuation of Ser. No. 375,442 filed May 6, 1982 (now abandoned), which itself is a continuation-in-part of U.S. patent application Ser. No. 226,366 filed Jan. 19, 1981 (now abandoned), which is a continuation of U.S. patent application Ser. No. 824,296 filed Aug. 15, 1977 (now U.S. Pat. No. 4,281,669) which itself is a continuation-in-part of U.S. patent application Ser. No. 683,382 filed May 5, 1976 (now U.S. Pat. No. 4,101,984).

FIELD OF INVENTION

The present invention relates to pacemaker electrodes.

BACKGROUND TO THE INVENTION

Three major problems which may be encountered with endocardial pacemaker electrodes during use are (1) a lack of stable position, (2) a chronic increase in stimulation threshold, and (3) a diminishing magnitude of the sensed endocardial signal. These problems are particularly manifested in the atrium, where maintenance of a stable anatomical position of the electrode has been a particularly difficult problem in the development of satisfactory endocardial leads for atrial pacing.

Another problem which is manifested in the blood stream by polished metal surfaces, such as are typically used in pacemaker electrodes, is the tendency to cause the formation of blood clots which may break loose and emobolize to various parts of the body.

SUMMARY OF INVENTION

In accordance with the present invention, there is provided an endocardial heart pacemaker electrode having a porous surface to permit tissue to form in the pores and at the surface thereof with a resulting tissue bond to the adjacent endocardium, thereby achieving a stable position of the electrode tip. In addition, the tissue formed at the surface provides a thin tissue covering on the exposed surface to render the same resistant to the formation of blood clots.

The fixation of the electrode in the atrium by tissue formation overcomes the problems of maintenance of a stable anatomical position characteristic of the prior art and enables low stimulation thresholds and a consistent magnitude of the sensed endocardial signal to be maintained.

The formation of the tissue coating on the exposed portions of the electrode surface with the consequent resistance of the surface to the formation of blood clots overcomes another difficulty of the prior art.

The electrode of the present invention is primarily designed for endocardial use for atrial pacemaking and is described with particular reference thereto. The electrode of the present invention, however, may also be used for endocardial ventricular or coronary sinus pacing.

The surface of the heart pacemaker electrode of this invention which engages the tissue is constructed of carbon. The electrode may be constructed wholly of carbon with the porous surface formed as an integral part thereof, or may be a composite of materials providing the carbon surface.

Carbon is an excellent conductor of electricity and is substantially inert to soft tissue, so that little or no reaction to the electrode occurs. These properties make carbon an excellent choice as the material of construction of a pacemaker electrode.

The combination of the physical attributes of the use of a carbon surface and the maintenance of a stable anatomical position by the use of the porous surface produces an implantable pacemaker electrode of superior properties.

GENERAL DESCRIPTION OF INVENTION

Figure 1:
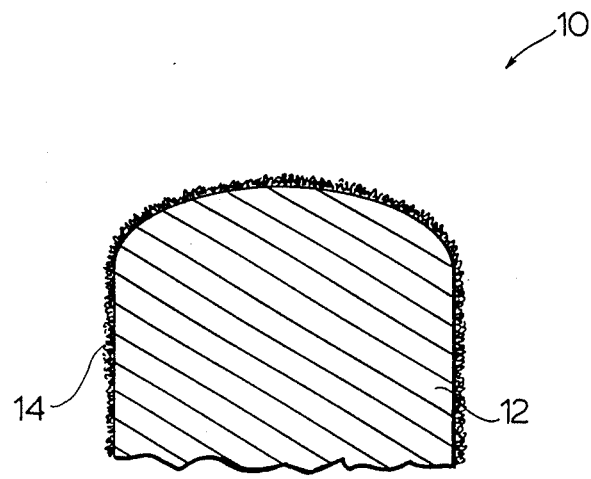
FIG. 1 is a part sectional view of a heart pacemaker electrode constructed in accordance with one embodiment of the invention.

In accordance with the present invention, it is essential that the electrode have a porous surface region constructed of carbon which permits tissue to form in the pores and bind the electrode to the endocardium or other adjacent tissue surface. The carbon may be in a native or activated form.

The porosity in the surface region may be provided in any convenient manner. For example, a plurality of pores may be formed in a solid carbon electrode, for example, by microfine drilling.

In another embodiment of the invention, the porous surface region may be provided by a fabric material, which is constructed of, impregnated with or coated with carbon material, bonded to a substrate.

The porous surface region may be in the form of carbon particles integrally joined into a matrix of interconnected pores with which the ingrowing tissue may interlock. Such a matrix of carbon particles may be bonded to or be integrally formed with a solid substrate of carbon or other material, or may constitute the electrode, whereby the electrode is wholly porous.

Such a matrix structure may be formed in any convenient manner, such as by pyrolyzing particles of a carbon precursor material, by sputtering, by plasma coating or by vapor deposition.

The pacemaker electrode of the invention may have any desired geometrical configuration conventional for pacemaker electrodes. For example, the electrode may have a cylindrical shape, in which case the overall length of the pacemaker electrode of the invention usually is about 0.1 to about 3 mm, preferably about 1 mm, and the diameter usually is also about 0.5 to about 5 mm, preferably about 2 mm. Such cylindrical electrodes may contain an insulating plug, usually of diameter of about 0.5 to about 3 mm, in the end thereof, which decreases the overall surface area of the electrode and is desirable under certain circumstances.

The electrode also may have a spherical shape, usually of diameter of about 0.5 to about 5 mm, preferably about 2 mm. The electrode may also include a cylindrical electrode sleeve positioned remote from the end of the lead, and may be used alone or in combination with a tip electrode. The electrode sleeve usually has an outside diameter of about 1 to about 5 mm, a thin wall usually of thickness of about 0.05 to about 0.3 mm, and a length of about 1 to about 10 mm, preferably about 3 mm.

The pore size of the pores in the porous surface of the electrode may vary widely but must be large enough to permit the growth of soft tissue into the pores and must be not so large that structural integrity is lost under the physiological stress of the body environment in which the electrode is located. Usually, the pore size of the pores is less than about 200 microns, preferably about 20 to about 100 microns.

As noted above, it is preferred that the porous surface be in communication with a network of interconnected pores in a subsurface. In such structure, the interstitial pore size is usually the same as the surface pore size while the porosity usually is about 10 to about 50% by volume.

The electrode may comprise a porous coating on a solid substrate. In such structure, the porous coating usually has a thickness of less than about 500 microns, preferably about 20 to about 300 microns.

The engagement of the porous surface region of the electrode with the blood stream in the atrium results in a controlled thrombotic reaction in which blood elements, including erythrocytes, platelets and leukocytes, accumulate in the pores and on the surface of the coating. Subsequent organization of the thrombus tissue, when in contact with the endocardium, results in the development of fibrous tissue within the pores and on the surface of the electrode with a resulting tissue bond to adjacent endocardium. This fibrous tissue is partially formed by colonization of nucleated cells circulating in the bloodstream onto the exposed porous surface and subsequent differentiation into other cell types which include fibrocytes, as well as direct ingrowth from the tissue in direct contact with the electrode.

The exposed portions of the porous surface of the electrode not in contact with the endocardium promotes the formation of a smooth, thin, adherent tissue covering on the porous surface, thereby rendering the same resistant to the formation of blood clots. The tissue coating is formed rapidly over a one to three month period and does not appear to increase significantly in thickness thereafter. This tissue response also represents organization of thrombus resulting in fibrous tissue formation within the pores and on the porous surface but the blood-contacting tissue consists of flattened endothelial-like cells which confer thromboresistance.

The formation of the fibrous tissue in the porous surface of the electrode with the consequent tissue bond to the endocardium fixedly locates the same in close proximity to the underlying myocytes, enabling consistently low chronic stimulation thresholds and a consistent magnitude of the sensed enocardial signal to be maintained. This result contrasts markedly with conventional leads which have smooth metal tips. The lack of stable fixation to the endocardium causes a tissue reaction and the formation of a thick tissue layer on the endocardium, widely separating the electrode from the myocardium, thereby causing an increase in stimulation threshold and decreased sensed endocardial signal during use.

DESCRIPTION OF PREFERRED EMBODIMENT

Referring to the drawing, a pacemaker electrode 10 has a generally cylindrical shape and comprises a coherent substrate 12 and a porous carbon coating 14 adhered thereto.

Figure 2:
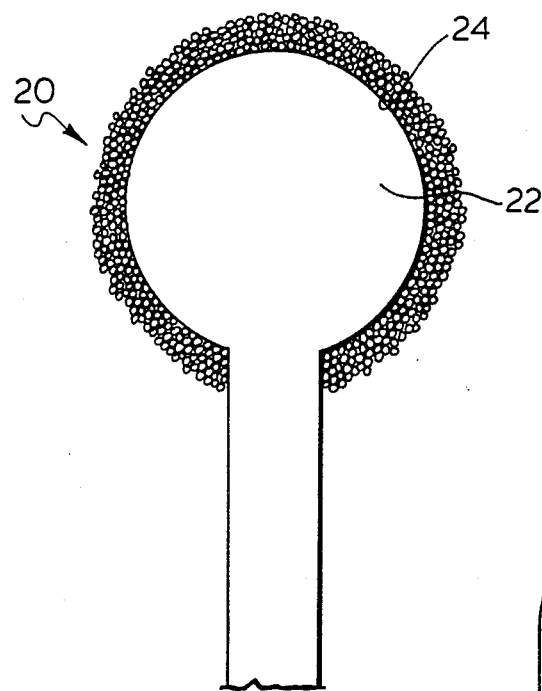
FIG. 2 is a part sectional view of a heart pacemaker electrode constructed in accordance with a second embodiment of the invention.
Figure 3:
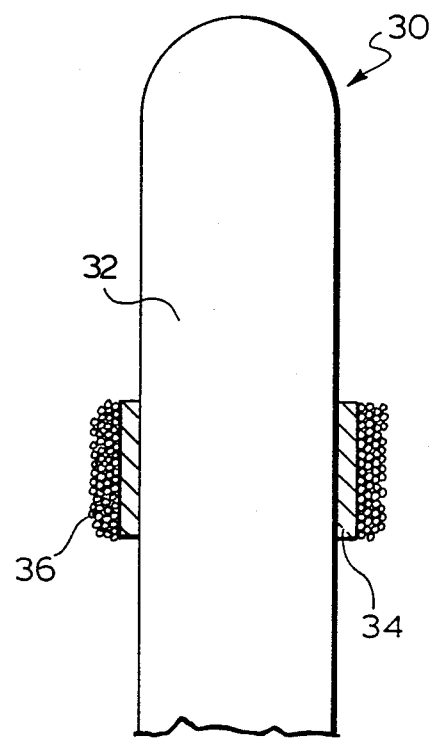
FIG. 3 is a part sectional view of a heart pacemaker electrode constructed in accordance with a third embodiment of the invention.

In FIG. 2, a pacemaker electrode 20 has a spherical shape and comprises a coherent substrate 22 and a porous carbon coating 24 adhered thereto. Similarly, in FIG. 3, a pacemaker electrode 30 has an elongate body 32, a cylindrical sleeve 34 mounted on the body and a porous carbon coating 36 adhered thereto.

SUMMARY OF DISCLOSURE

In summary of this disclosure, the present invention provides a pacemaker electrode of improved construction. Modifications are possible within the scope of this invention.

What I claim is:

1. An endocardial pacemaker electrode for endocardial atrial and ventricular pacing, said electrode having a regular geometrical shape, a maximum transverse dimension of about 0.1 to about 5 mm and a minimum longitudinal dimension of at least about 0.1 mm, said electrode being formed of a composite of materials comprising a porous carbon coating of thickness less than 500 microns on a substrate of material other than carbon providing an external surface which is constructed of carbon and which has pores therein which permit the ingrowth of tissue into the porous coating and which have a size less than about 200 microns.

2. The electrode of claim 1 wherein said porous coating includes a network of interconnected pores of porosity of about 10 to about 50% communicating with the pores in said external surface.

3. The electrode of claim 2 wherein said porous coating has a thickness of about 20 to about 300 microns.

4. The pacemaker electrode of claim 1 wherein said pore size is about 20 to about 100 microns.

5. The electrode of claim 1 wherein the electrode has a cylindrical shape having a length of about 0.1 to about 3 mm and a diameter of about 0.5 to about 5 mm.

6. The electrode of claim 1 wherein the electrode has a spherical shape of diameter of about 0.5 to about 5 mm.

7. The electrode of claim 1 wherein the electrode comprises a cylindrical electrode sleeve having an outside diameter of about 1 to about 5 mm, a thin wall of thickness of about 0.05 to about 0.3 mm and a length of about 1.6 to about 10 mm.

* * * * *